(12) United States Patent
St. Pierre et al.

(10) Patent No.: US 7,488,339 B2
(45) Date of Patent: Feb. 10, 2009

(54) MULTILAYER MEDICAL DEVICE

(75) Inventors: Ernest J. St. Pierre, South Attleboro, MA (US); Ronald A. Sahatjian, Lexington, MA (US); Peter L. Dayton, Brookline, MA (US); David Vafiades, Bedford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 480 days.

(21) Appl. No.: 10/274,633

(22) Filed: Oct. 21, 2002

(65) Prior Publication Data

US 2004/0078052 A1 Apr. 22, 2004

(51) Int. Cl.
*A61M 29/00* (2006.01)

(52) U.S. Cl. ...................... 606/194; 604/103

(58) Field of Classification Search .......... 604/103, 604/103.05, 103.06; 606/192, 194
See application file for complete search history.

(56) References Cited

U.S. PATENT DOCUMENTS

| | | | |
|---|---|---|---|
| 3,561,493 A | 2/1971 | Maillard et al. |
| 3,618,614 A | 11/1971 | Flynn |
| 3,924,634 A | 12/1975 | Taylor et al. |
| 3,993,812 A | 11/1976 | Debbas et al. |
| 4,044,180 A | 8/1977 | Baker |
| 4,047,868 A | 9/1977 | Kudo et al. |
| 4,079,850 A | 3/1978 | Suzuki et al. |
| 4,174,783 A | 11/1979 | Abe et al. |
| 4,182,457 A | 1/1980 | Yamada et al. |
| 4,211,741 A | 7/1980 | Ostoich |
| 4,244,914 A | 1/1981 | Ranalli et al. |
| 4,282,876 A | 8/1981 | Flynn |
| 4,296,156 A | 10/1981 | Lustig et al. |
| 4,327,736 A | 5/1982 | Inoue |
| 4,335,723 A | 6/1982 | Patel |
| 4,409,364 A | 10/1983 | Schmukler et al. |
| 4,424,242 A | 1/1984 | Barbee |
| 4,472,129 A | 9/1984 | Siard |
| 4,484,971 A | 11/1984 | Wang |
| 4,490,421 A | 12/1984 | Levy |
| 4,551,292 A | 11/1985 | Fletcher et al. |
| 4,578,024 A | 3/1986 | Sicka et al. |
| 4,596,563 A | 6/1986 | Pande |
| 4,627,844 A | 12/1986 | Schmitt |
| 4,634,615 A | 1/1987 | Versteegh et al. |
| 4,636,346 A | 1/1987 | Gold et al. |
| 4,636,442 A | 1/1987 | Beavers et al. |

(Continued)

FOREIGN PATENT DOCUMENTS

DE 28 48 854 5/1979

(Continued)

OTHER PUBLICATIONS

Rigid Plastics Are Getting a Foot in the Kitchen Door, Chemicalweek, McGraw-Hill Publication, Oct. 12, 1983.

(Continued)

*Primary Examiner*—Kevin T Truong
*Assistant Examiner*—Victor X Nguyen
(74) *Attorney, Agent, or Firm*—Crompton, Seager & Tufte, LLC

(57) ABSTRACT

Multilayer medical devices, apparatuses for making such devices, and methods of making such devices are disclosed.

55 Claims, 2 Drawing Sheets

U.S. PATENT DOCUMENTS

| | | | |
|---|---|---|---|
| 4,640,852 A | 2/1987 | Ossian |
| 4,648,871 A | 3/1987 | Jacob |
| 4,656,070 A | 4/1987 | Nyberg et al. |
| 4,677,017 A | 6/1987 | DeAntonis et al. |
| 4,686,124 A | 8/1987 | Onohara et al. |
| 4,753,765 A | 6/1988 | Pande |
| 4,778,697 A | 10/1988 | Genske et al. |
| 4,790,831 A | 12/1988 | Skribiski |
| 4,814,231 A | 3/1989 | Onohara et al. |
| 4,816,339 A | 3/1989 | Tu et al. |
| 4,818,592 A | 4/1989 | Ossian |
| 4,824,618 A | 4/1989 | Strum et al. |
| 4,834,721 A | 5/1989 | Onohara et al. |
| 4,840,623 A | 6/1989 | Quackenbush |
| RE32,983 E | 7/1989 | Levy |
| 4,863,426 A | 9/1989 | Ferragamo et al. |
| 4,880,682 A | 11/1989 | Hazelton et al. |
| 4,906,244 A | 3/1990 | Pinchuk et al. |
| 4,917,088 A | 4/1990 | Crittenden |
| 4,932,956 A | 6/1990 | Reddy et al. |
| 4,952,357 A | 8/1990 | Euteneuer |
| 4,963,306 A | 10/1990 | Weldon |
| 4,994,047 A | 2/1991 | Walker et al. |
| 5,041,089 A | 8/1991 | Mueller et al. |
| 5,059,269 A | 10/1991 | Hu et al. |
| 5,071,686 A | 12/1991 | Genske et al. |
| 5,076,776 A | 12/1991 | Yamada et al. |
| 5,093,164 A | 3/1992 | Bauer et al. |
| 5,094,799 A | 3/1992 | Takashige et al. |
| 5,100,721 A | 3/1992 | Akao |
| 5,108,415 A | 4/1992 | Pinchuk et al. |
| 5,125,913 A | 6/1992 | Quackenbush |
| 5,156,857 A | 10/1992 | Wang et al. |
| 5,171,221 A | 12/1992 | Samson |
| 5,195,969 A | 3/1993 | Wang et al. |
| 5,201,706 A | 4/1993 | Noguchi et al. |
| 5,223,205 A | 6/1993 | Jackowski et al. |
| 5,254,090 A | 10/1993 | Lombardi et al. |
| 5,270,086 A | 12/1993 | Hamlin |
| 5,277,199 A | 1/1994 | DuBois et al. |
| 5,290,306 A | 3/1994 | Trotta et al. |
| 5,304,197 A | 4/1994 | Pinchuk et al. |
| 5,306,246 A | 4/1994 | Sahatjian et al. |
| 5,318,041 A | 6/1994 | DuBois et al. |
| 5,330,428 A | 7/1994 | Wang et al. |
| 5,330,429 A | 7/1994 | Noguchi et al. |
| 5,344,401 A | 9/1994 | Radisch et al. |
| 5,356,709 A | 10/1994 | Woo et al. |
| 5,358,486 A | 10/1994 | Saab |
| 5,366,442 A * | 11/1994 | Wang et al. ............ 604/103 |
| 5,417,671 A | 5/1995 | Jackson |
| 5,427,842 A | 6/1995 | Bland et al. |
| 5,439,454 A | 8/1995 | Lo et al. |
| 5,478,320 A | 12/1995 | Trotta |
| 5,509,899 A | 4/1996 | Fan et al. |
| 5,512,051 A | 4/1996 | Wang et al. |
| 5,556,383 A | 9/1996 | Wang et al. |
| 5,562,127 A | 10/1996 | Fanselow et al. |
| 5,587,125 A * | 12/1996 | Roychowdhury ............ 264/515 |
| 5,613,979 A | 3/1997 | Trotta et al. |
| 5,620,649 A | 4/1997 | Trotta |
| 5,669,920 A | 9/1997 | Conley et al. |
| 5,755,690 A | 5/1998 | Saab |
| 5,769,817 A | 6/1998 | Burgmeier |
| 5,792,105 A * | 8/1998 | Lin et al. ............ 604/103.01 |
| 5,797,877 A | 8/1998 | Hamilton et al. |
| 5,820,594 A | 10/1998 | Fontirroche et al. |
| 5,824,173 A | 10/1998 | Fontirroche et al. |
| 5,833,657 A | 11/1998 | Reinhardt et al. |
| 5,843,032 A | 12/1998 | Kastenhofer |
| 5,851,464 A | 12/1998 | Davila et al. |
| 5,871,468 A | 2/1999 | Kramer et al. |
| 5,879,369 A | 3/1999 | Ishida |
| 5,908,406 A | 6/1999 | Ostapchenko et al. |
| 5,961,765 A | 10/1999 | Kastenhofer |
| 6,004,289 A | 12/1999 | Saab |
| 6,010,521 A | 1/2000 | Lee et al. |
| 6,027,477 A | 2/2000 | Kastenhofer |
| 6,059,751 A | 5/2000 | Ostapchenko et al. |
| 6,086,556 A | 7/2000 | Hamilton et al. |
| 6,124,007 A | 9/2000 | Wang et al. |
| 6,132,824 A | 10/2000 | Hamlin |
| 6,136,258 A | 10/2000 | Wang et al. |
| 6,136,394 A | 10/2000 | Karsten |
| 6,165,166 A | 12/2000 | Samuelson et al. |
| 6,242,063 B1 * | 6/2001 | Ferrera et al. ............ 428/35.2 |
| 6,319,228 B1 | 11/2001 | Kastenhofer |
| 6,335,101 B1 | 1/2002 | Haeger et al. |
| 6,343,919 B1 | 2/2002 | Rodriguez et al. |
| 6,444,324 B1 | 9/2002 | Yang et al. |
| 6,447,835 B1 | 9/2002 | Wang et al. |
| 6,464,683 B1 | 10/2002 | Samuelson et al. |
| 6,471,673 B1 | 10/2002 | Kastenhofer |
| 6,482,348 B1 | 11/2002 | Wang et al. |
| 6,488,655 B1 | 12/2002 | Wantink et al. |
| 6,951,675 B2 | 10/2005 | Chin et al. |
| 2001/0043998 A1 | 11/2001 | Chen et al. |
| 2002/0165523 A1 | 11/2002 | Chin et al. |
| 2004/0078052 A1 | 4/2004 | St. Pierre et al. |
| 2005/0266109 A1 | 12/2005 | Chin et al. |

FOREIGN PATENT DOCUMENTS

| | | |
|---|---|---|
| DE | 36 38 828 | 5/1988 |
| DE | 3638828 | 5/1988 |
| EP | 0 095 521 A1 | 12/1983 |
| EP | 0 101 213 | 2/1984 |
| EP | 0 201 331 | 11/1986 |
| EP | 0 174 206 | 12/1986 |
| EP | 0 201 331 | 12/1986 |
| EP | 0 276 908 | 8/1988 |
| EP | 0 292 587 | 11/1988 |
| EP | 0 420 488 | 4/1991 |
| EP | 0 428 479 | 5/1991 |
| EP | 0 457 456 | 11/1991 |
| EP | 0 461 474 | 12/1991 |
| EP | 0803264 A1 | 10/1997 |
| FR | 998.035 | 1/1952 |
| FR | 2 328 482 | 5/1977 |
| GB | 1 556 242 | 10/1976 |
| GB | 1 533 204 | 9/1977 |
| GB | 1 600 963 | 5/1978 |
| GB | 2 077 111 | 6/1980 |
| GB | 2 078 114 | 12/1981 |
| GB | 2 140 437 | 11/1984 |
| GB | 2 163 386 | 2/1986 |
| JP | 51-084877 | 7/1976 |
| JP | 53-045353 | 12/1978 |
| JP | 53-45353 | 12/1978 |
| JP | 8045-353 | 12/1978 |
| JP | 58-038778 | 3/1983 |
| JP | 58038778 | 3/1983 |
| JP | 02-043036 | 2/1990 |
| JP | 2-43036 | 2/1990 |
| JP | 3-277374 | 12/1991 |
| JP | 04-034590 | 2/1992 |
| JP | 4-34590 | 2/1992 |
| JP | 4-259537 | 9/1992 |
| SU | 1477423 | 5/1989 |
| WO | WO 84/01327 | 4/1984 |
| WO | WO 91/04068 | 4/1991 |
| WO | WO 92/11893 | 7/1992 |
| WO | WO92/19316 | 11/1992 |
| WO | WO96/04951 | 2/1996 |

| | | |
|---|---|---|
| WO | WO97/32624 | 9/1997 |
| WO | WO 99/12586 | 3/1999 |
| WO | WO 01/32398 | 5/2001 |

OTHER PUBLICATIONS

Developments in Cast and Blown Film, Plastic Technology, Aug. 1987, vol. 33 #9, p. 39 & 41.
William J. Broad, Plastics Revolution: A Rush of New Uses, The New York Times, Science Times, Tuesday, Nov. 1, 1983.
The Gamma bottle, Food & Drug Packaging, Oct. 1988, p. 34-36.
Squeezable bottle ends long wait for ketchup, Food & Drug Packaging, Oct. 1983, vol. 47, #10.
Extruded tubing is called on to perform more complex and critical surgical jobs, Modern Plastics International, Apr. 1990, p. 40-41.
Christopher Irwin, Blow Molding, Modern Plastics Encyclopedia, 1988, p. 203-210.
International Search Report received in PCT Application No. PCT/US01/40220, mailed Sep. 23, 2002.
International Search Report received in PCT Application No. PCT/US04/001672, dated Jun. 16, 2004.
Examination Report received in EP Application No. 03 742 393.3, dated Nov. 17, 2006.
International Search Report dated Sep. 23, 2002.

* cited by examiner

MULTILAYER MEDICAL DEVICE

TECHNICAL FIELD

This invention relates to multilayer medical devices, such as multi-layer balloons.

BACKGROUND

Medical procedures can utilize a balloon in different ways. As an example, in some procedures a balloon is used to open an occluded lumen, as in angioplasty. As another example, in certain procedures a balloon is used to position another medical implement, such as a stent or graft, within a lumen. As an additional example, a balloon is used to selectively block a passageway. In additional examples, a balloon is used in various combinations of these procedures.

In some cases, the balloon is positioned on the end of a catheter shaft. The balloon is typically wrapped around the catheter shaft to reduce the radial profile for easier insertion. The catheter is then threaded through the body to position the balloon at a location of treatment and the balloon is inflated. Finally, the balloon is deflated and the catheter is withdrawn from the body.

SUMMARY

The invention relates to multi-layer medical devices, such as multi-layer balloons.

In one aspect, the invention features a medical device having a wall. The wall includes a first layer including a polyester or a polyester copolymer, a second layer including a polyamide or a polyamide copolymer, and a third layer including an adhesive material. The first, second and third layers are coextruded.

In another aspect, the invention features a medical device having a wall. The wall includes a first layer including a polyester or a polyester copolymer, a second layer including a polyamide or a polyamide copolymer, and a third layer including an adhesive material. The thickness of the first layer is at least about 50 percent of a total thickness of the wall.

In a further aspect, the invention features a medical device having a wall. The wall includes a first layer including a polyester or a polyester copolymer, a second layer including a polyamide or a polyamide copolymer, and a third layer including an adhesive material. The thickness of the third layer is less than about 20 percent of a total thickness of the wall.

In one aspect, the invention features a medical device having a wall. The wall includes a first layer including a polyester or a polyester copolymer, a second layer including a polyamide or a polyamide copolymer, and a third layer including an adhesive material. The third layer is less than about 0.005 inch thick.

In another aspect, the invention features a method of forming a tube. The method includes coextruding first second and third materials to form a wall of the tube with first, second and third layers. The first layer includes a polyester or a polyester copolymer. The second layer includes a polyamide or a polyamide copolymer, and the third layer includes an adhesive material.

In a further aspect, the invention features a method of forming a tube. The method includes coextruding multiple polymer layers to form a wall of the tube, and forming the tube into a balloon. The method also includes heating the balloon to a temperature of at least about 50° C. at a pressure of at least about 50 pounds per square inch.

In one aspect, the invention features an extrusion apparatus. The apparatus includes at least three extruders, and a cross-head in fluid communication with the extruders. The cross-head is capable of holding from about 3.2 cubic centimeters to about five cubic centimeters of a fluid from one of the first extruders.

In another aspect, the invention features an extrusion apparatus that includes a at least three extruders, and a cross-head in fluid communication with the extruders. The cross-head is capable of holding from about two cubic centimeters to about four cubic centimeters of a fluid from one of the extruders.

In a further aspect, the invention features an extrusion apparatus that includes at least three extruders, and a cross-head in fluid communication with the first, second and third extruders. The cross-head is capable of holding from about three cubic centimeters to about 4.5 cubic centimeters of a fluid from one of the extruders.

In certain embodiments, the coextruded polymer wall structure can provide a medical device, such as a balloon, with desirable properties. For example, the medical device can exhibit good hoop strength, toughness, crack resistance, compliance, resistance to delamination and resistance to pinhole formation, while at the same time providing relatively high burst strength and desired dispensability, typically using substantially crystalline, biaxially oriented polymers. While such properties can be advantageous for any size medical device, the properties can be particularly advantageous for relatively large balloons (e.g., balloons having an inflated diameter of more than about four millimeters, such as more than about 4.25 millimeters, more than about 4.5 millimeters).

In some embodiments, the medical device (e.g., balloon) can undergo no substantial physical degradation when subjected to conditions that are as stressful or more stressful than the intended use conditions of the medical device.

Features, objects and advantages of the invention are in the description, drawings and claims.

DETAILED DESCRIPTION

Figure 1:
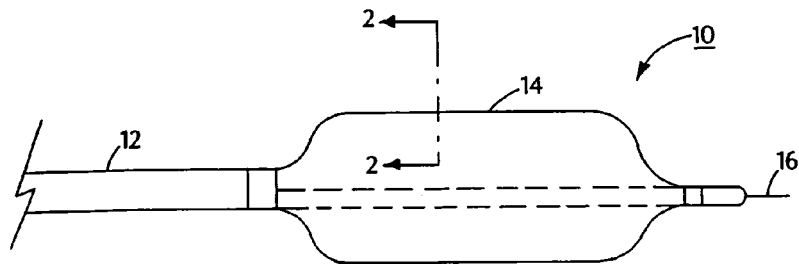
FIG. 1 is a side view of an embodiment of a balloon catheter system.

FIG. 1 shows an embodiment of a balloon catheter system 10 including a catheter shaft 12 carrying an inflatable multi-layer balloon 14. A guide wire 16 can be used to deliver balloon 14 to a treatment area (e.g., a coronary artery). Examples of catheter systems are described in, for example, U.S. Pat. Nos. 5,195,969 and 5,270,086, which are hereby incorporated by reference. An example of a balloon catheter system is the Ranger® system, commercially available from Boston Scientific Scimed, Maple Grove, Minn.

Figure 2:
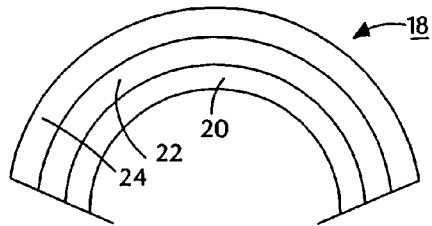
FIG. 2 is a cross-section through a section of a wall of a multi-layer balloon taken along the line 2-2 in FIG. 1.

FIG. 2 is a cross-sectional view of a wall 18 of balloon 14. Wall 18 includes coextensively coextruded polymer layers

20, 22 and 24, which are formed of a polyester, an adhesive and a polyamide, respectively.

In general, layer 20 can be formed of any polyester-containing material (e.g., a substantially pure polyester, a blend containing at least one polyester, a polyester copolymer) appropriate for use in a medical device. Such polymers include, for example, polyester homopolymers and/or copolymers (e.g., block copolymers) of polyesters. Examples of polyesters include the polyethylene terephthalate (PET) polymers, polybutylene terephthalate (PBT) polymers and blends and combinations thereof. Examples of commercially available polyesters include the Selar PT family of polymers (e.g., Selar PT 8307, Selar PT4274, Selar PTX280), which are commercially available from E. I. DuPont de Nemours (Wilmington, Del.), the Cleartuf family of polymers (e.g., Cleartuf 8006), which are commercially available from M&G Polymers (Apple Grove, W. Va.), the Traytuf family of polymers (e.g., Traytuff 1006), which are commercially available from the Shell Chemical (Houston, Tex.), the Melinar family of polymers, commercially available from E. I. DuPont de Nemours (Wilmington, Del.), the Celanex family of polymers, commercially available from Ticona (Summit, N.J.), the Riteflex family of polymers, commercially available from Ticona (Summit, N.J.), the Hytrel family of polymers (e.g., Hytrel 5556, Hytrel 7246, Hytrel 4056), commercially available from E. I. DuPont de Nemours (Wilmington, Del.), and the Arnitel family of polymers (e.g., Arnitel EM630), commercially available from DSM (Erionspilla, Ind.).

Generally, layer 22 can be formed any adhesive material appropriate for use in a medical device. Typically, the adhesive is a polymer (e.g., a substantially pure polymer, or a blend of polymers). In general, an adhesive refers to a material that is capable of forming a bond with its adjacent layers of materials so that the resulting multilayer device (e.g., a medical device, such as a tube or balloon catheter) can be used for its intended purpose. Preferred adhesive materials maintain their desired adhesive properties (e.g., undergo substantially no chemical degradation) when exposed to process conditions described herein. As an example, in certain embodiments, layer 22 is formed of an ethylene vinyl acetate polymer-containing material, such as a functionalized ethylene vinyl acetate copolymer (e.g., an ethylene vinyl acetate copolymer containing maleic anhydride groups, an ethylene vinyl acetate copolymer containing glycidyl methacrylate groups). As another example, in some embodiments, layer 22 is formed of an anhydride-modified polyolefin. An adhesive can be selected, for example, from the Bynel family of polymers (e.g., Bynel CXA Series, Bynel 1000 Series, Bynel 1123, Bynel 1124, Bynel 11E554, Bynel 11E573, Bynel CXA E-418), commercially available from E. I. DuPont de Nemours (Wilmington, Del.), the Plexar family of polymers (e.g., PX360, PX360E, PX380, PX3227, PX3236, PX3277, PX5125, PX5327, PX206, PX209, PX2049, PX165, PX175, PX180, PX909, PX101, PX107A, PX108, PX114, PX1164), commercially available from Equistar Chemicals (Newark, N.J.), and/or the BLOX family of polymers (e.g., BLOX 200 Series), commercially available from the Dow Chemical Company (Midland, Mich.).

In general, layer 24 can be formed of any polyamide-containing material (e.g., a substantially pure polyamide, a blend containing at least one polyamide) appropriate for use in a medical device. Such polymers include, for example, polyamide homopolymers and/or copolymers (e.g., block copolymers) of polyamides. One type of polyamide includes the nylon family of polymers, including, for example, aliphatic nylons and aromatic nylons. A nonlimiting list of exemplary nylons includes Nylon 12, commercially available from Atofina (Philadelphia, Pa.), Nylon 6, commercially available from Honeywell (Morristown, N.J.), Nylon 6/10, commercially available from BASF (Mount Olive, N.J.), Nylon 6/12, commercially available from Ashley Polymers (Cranford, N.J.), Nylon 11, Nylon MXD-6, the Grivory family of polymers, commercially available from EMS (Sumter, S.C.), the Grilamid family of polymers, commercially available from EMS (Sumter, S.C.), and the Vestamid family of polymers, commercially available from Daicel-Degussa Ltd. Additional polyamides include the Pebax family of polymers (e.g., Pebax 5533, Pebax 2533, Pebax 7033), commercially available from Atofina (Philadelphia, Pa.) and the Trogamid family from Daicel-Degussa.

One or more of the layers of wall 18 can contain additional material(s). For example, one or more layers of wall 18 can contain one or more additional polymers (e.g., blended therewith), such as liquid crystal polymer(s) (LCPs), polyester(s), polyamide(s), and/or their copolymers. Examples of such materials include the Vectra family of polymers (e.g., Vectra A, Vectra B, Vectra LKX, Vectra LKX 1111) and the Vectran family of polymers (e.g. Vectran V300P), both commercially available from Ticona (Summit, N.J.), acrylonitrile-butadiene-styrenes (ABSs), ABS/nylon, ABS/polyvinyl chlorides (PVCs), ABS/polycarbonate, acrylonitrile copolymers, polyacrylates, polyacrylsulfones, polyethylene naphthalates (PENs), polyetheretherketones (PEEKs), polyethersulfones (PESs), polyetherimides (PEIs), polyetherketones (PEKs), polymethylpentenes, polyphenylene ether, polyphenylene sulfides styrene acrylonitriles (SANs), propylene ethylene vinylacetate, ethylene vinyl alcohols (EVAs), ionomeric polymers, polyethylene type I-IVs, polyolefins, polyurethanes, PVCs, polysiloxanes (silicones), fluorocarbons, such as polychlorotrifluoroethylenes (CTFEs), poly[ethylenecochlorotrifluoroethylene]s (ECTFEs) copolymer ethylene tetrafluoroethylenes (ETFEs), copolymer tetrafluoroethylenes, hexafluoropropylenes (FEPs), perfluoroalkanes (PFAs), and poly[vinylidene fluoride]s (PVDF)s.

The thickness of layers 20, 22 and 24 can be varied as desired.

In certain embodiments, the thickness of layer 20 is at least about 50 percent (e.g., at least about 60 percent, at least 70 percent, at least 80 percent) of the total thickness of wall 18. In some embodiments, the thickness of layer 20 is less than about 90 percent (e.g., less than about 80 percent, less than about 70 percent, less than about 60 percent) of the total thickness of wall 18.

In certain embodiments, the thickness of layer 24 is at least about one percent (e.g., at least about two percent, at least about five percent, at least about 10 percent, at least about 20 percent, at least about 30 percent, at least about 40 percent) of the total thickness of wall 18. In some embodiments, the thickness of layer 24 is less than about 50 percent (e.g., less than about 40 percent, less than about 30 percent, less than about 20 percent, less than about 10 percent, less than about five percent, less than about two percent) of the total thickness of wall 18.

In some embodiments, layer 22 has a thickness of less than about 0.005 inch (e.g., less than about 0.004 inch, less than about 0.003 inch, less than about 0.002 inch, less than about 0.001 inch, less than about 0.0005 inch, less than about 0.0004 inch, less than about 0.0003 inch, less than about 0.0002 inch, less than about 0.0001 inch, less than about 0.00005 inch).

In general, the balloons can be of any desired shape and size (e.g., coronary balloons, aortic balloons, peripheral balloons, reperfusion balloons, endoscopy balloons, urology balloons and neurology balloons). In certain embodiments, a coronary balloon can have a diameter of from about 1.5 millimeters to about six millimeters. In some embodiments, a peripheral balloon can have a diameter of from about three millimeters to about 12 millimeters. In certain embodiments, an endoscopy and/or urology balloon can have a diameter of from about four millimeters to about 40 millimeters. In some embodiments, a neurology balloon can have a diameter of from about 1.5 millimeters to about five millimeters.

The balloon can have a diameter of, for example, at least about one millimeters (e.g., at least about two millimeters, at least about three millimeters). In certain embodiments, the balloons have a relatively large diameter (e.g., at least about four millimeters, at least about five millimeters, at least about six millimeters, at least about seven millimeters, at least about eight millimeters, at least about nine millimeters, at least about 10 millimeters, at least about 11 millimeters, at least about 12 millimeters, at least about 20 millimeters, at least about 30 millimeters, at least about 40 millimeters).

In some embodiments, the balloon can have a relatively high burst pressure. For example, the balloon can have a burst pressure of at least about 200 psi (e.g., at least about 225 psi, at least about 250 psi, at least about 275 psi, at least about 300 psi, at least about 325 psi, at least about 350 psi, at least about 375 psi, at least about 400 psi, at least about 425 psi, at least about 450 psi). As referred to herein, the burst pressure of a balloon is determined as follows. The balloon is deflated and submerged in a water bath at 37° C. The balloon is then inflated with water at a rate of about 20 psi per second until the balloon bursts.

In certain embodiments, the balloon can have a relatively high degree of compliance. For example, the balloon can have a compliance of at least about two percent (e.g., at least about 2.25%, at least about 2.5%, at least about 2.75%, at least about three percent, at least about 3.25%, at least about 3.5%). As referred to herein, the degree of compliance of a balloon is determined as follows. The balloon is held at 37° C. and inflated first to one atmosphere pressure, and then in increments of one atmosphere pressure while measuring the diameter of the balloon. This is done until the balloon reaches the rated burst pressure or until the balloon bursts. A plot of the results is generated, the slope from four atmospheres pressure to the rated burst pressure is calculated, and is the compliance value (diameter versus pressure).

Figure 3:
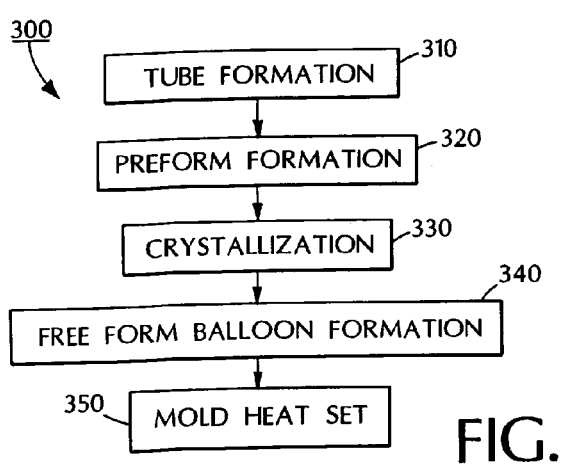
FIG. 3 is a schematic diagram of steps in an embodiment of a process for forming a balloon.

FIG. 3 is a schematic diagram showing steps in a process 300 for making balloon 14. In a step 310, layers 20, 22 and 24 are coextensively coextruded to form a tube. According to a step 320, a preform is formed from the tube. Layers 20, 22 and 24 in the preform are crystallized (e.g., biaxially oriented) during a step 330. In a step 340, a free form balloon is prepared, and the balloon is optionally subjected to a mold heat set in step 350.

Without wishing to be bound by theory, it is believed that making the coextruded balloons with appropriate physical properties (e.g., good hoop strength, layer adhesion, toughness, and/or crack resistance and resistance to pinhole formation) can involve using an extrusion apparatus and/or extrusion conditions that provide a residence time and adequate pressure for the polymers that is sufficient for appropriate adhesion to occur between the polymer layers but not so severe so that the polymers undergo undesirable degradation, particularly the adhesive layer material(s).

Figure 4:
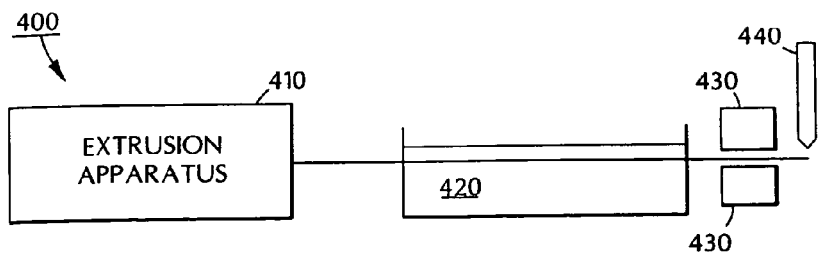
FIG. 4 is a schematic diagram of steps in an embodiment a process for forming a tube.

FIG. 4 is a schematic diagram of a system 400 used during step 310 of process 300. System 400 includes an extrusion apparatus 410, a cooling bath 420, a take-off apparatus 430, and a cutter 440. Typically, during tube formation, the material(s) from which layers 20, 22 and 24 are dried and then added to pre-heated extrusion apparatus 410. The materials are allowed to melt and a force is applied to the materials to cause them to be coextensively coextruded into the shape of a tube, and to cause the tube-shaped, coextruded materials exit extrusion apparatus 410. Take-off apparatus 430 draws the tube through bath 420, where the tube is cooled, and then draws the cooled tube to cutter 440, where the tubes are cut into desired lengths.

Figure 5:
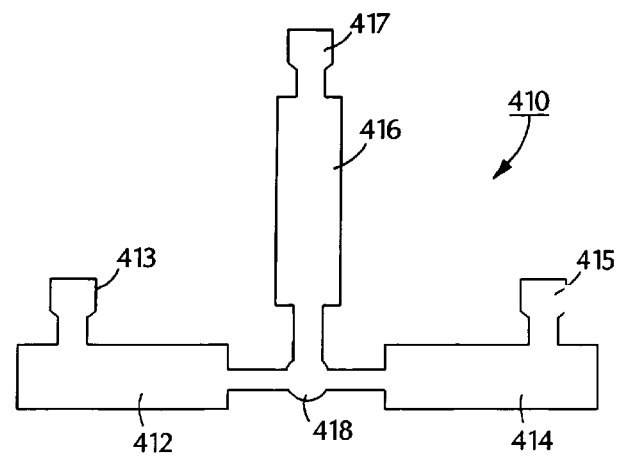
FIG. 5 is a schematic view of an embodiment of an extrusion apparatus.

FIG. 5 is a schematic representation of an embodiment of extrusion apparatus 410 having extruders 412, 414 and 416, and a cross-head 418. Extruders 412, 414 and 416 have hoppers 413, 415 and 417, respectively.

Figure 6:
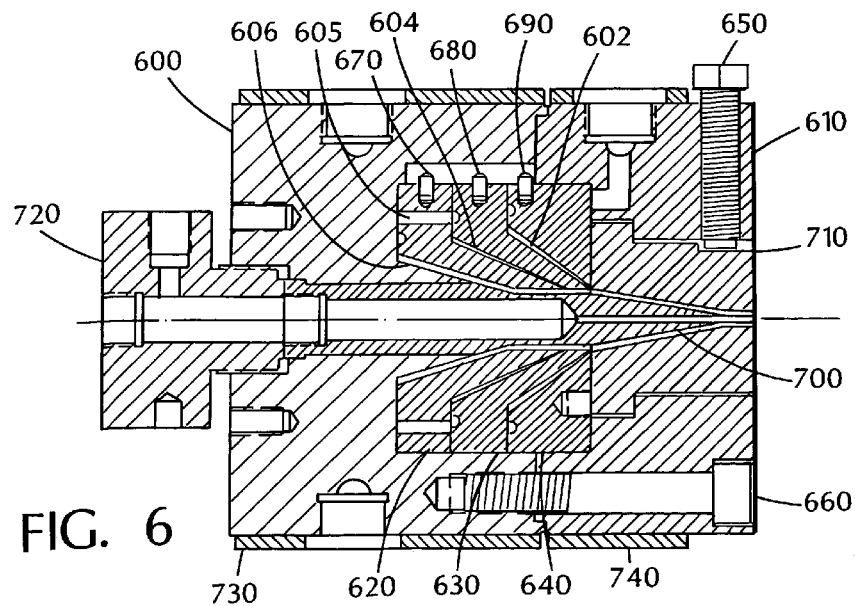
FIG. 6 is a cross-sectional view of an embodiment of a cross-head.

FIG. 6 is a cross-sectional view of an embodiment of a cross-head 418. Cross-head 418 has a body 600, a die retainer 610, an inner layer flow divider 620, a middle layer flow divider 630, an outer layer flow divider 640, bolts 650 and 660, divider alignment pins 670, 680 and 690, a tip 700, a die 710, a tip retainer 720, a body heater 730 and a die retainer heater 740.

In certain embodiments, the respective volumes of cross-head 418 that contain the material(s) that form layers 20, 22 and 24 can be relatively small. For each layer, the volume of cross-head 418 that contains the corresponding material(s) includes a thin portion between the corresponding flow dividers (volume 606 for layer 20, volume 604 for layer 22, and volume 602 for layer 24). For each layer, the volume of cross-head 418 that contains the material(s) that form the corresponding layer further includes an additional feed channel volume. The volume in cross-head 418 for the material of layer 22 includes a feed channel volume 605. (The corresponding feed channel volumes for layers 20 and 24 are not visible in the cross-section in FIG. 6). Appropriately designed extrusion apparatuses are available from, for example, Guil Tool and Engineering (West Warwick, R.I.).

As an example, the volume of cross-head 418 that contains the material(s) from layer 20 is formed is at least about three cubic centimeters (e.g., at least about 3.2 cubic centimeters, at least about 3.4 cubic centimeters) and/or less than about five cubic centimeters (e.g., less than about 4.5 cubic centimeters, less than about four cubic centimeters). As another example, the of cross-head 418 that contains the material(s) from layer 22 is formed is at least about two cubic centimeters (e.g., at least about 2.2 cubic centimeters, at least about 2.4 cubic centimeters) and/or less than about four cubic centimeters (e.g., less than about 3.5 cubic centimeters, less than about three cubic centimeters). As an additional example, the volume of cross-head 418 that contains the material(s) from layer 24 is formed is at least about three cubic centimeters (e.g., at least about 3.3 cubic centimeters, at least about 3.6 cubic centimeters) and/or less than about 4.5 cubic centimeters (e.g., less than about 4.4 cubic centimeters, less than about 4.3 cubic centimeters).

Typically, extruders 412, 414 and 416 are pre-heated to a desired temperature. For example, extruder 412 may be pre-heated to a temperature of at least about 230° C. and/or less than about 315° C. (e.g., from about 260° C. to about 300° C., from about 275° C. to about 290° C.), extruder 414 may be pre-heated to a temperature of at least about 175° C. and/or less than about 230° C. (e.g., from about 190° C. to about 210° C., about 200° C.), and/or extruder 416 may be pre-heated to a temperature of at least about 190° C. and/or less than about 245° C. (e.g., from about 200° C. to about 225° C., about 200° C.). In certain embodiments, extruders 412, 414 and 416 are used to extrude layers 20, 22 and 24, respectively, using these temperatures.

The pressure applied to the melted material(s) in extruders 412, 414 and 416 can be varied as desired. As an example, the pressure applied to the melted material(s) in extruder 412 can be at least about 500 psi (e.g., at least about 1,000 psi, at least about 1,500 psi) and/or less than about 4,000 psi (e.g., less than about 3,000 psi, less than about 2,500 psi), the pressure applied to the melted material(s) in extruder 414 can be at least about 300 psi (e.g., at least about 400 psi, at least about 500 psi) and/or less than about 3,000 psi (e.g., less than about 2,000 psi, less than about 1,500 psi), the pressure applied to the melted material(s) in extruder 416 can be at least about 200 psi (e.g., at least about 300 psi, at least about 400 psi) and/or less than about 1,000 psi (e.g., less than about 900 psi, less than about 800 psi). In certain embodiments, extruders 412, 414 and 416 are used to extrude layers 20, 22 and 24, respectively, using these pressures.

Generally, the temperature of bath 460 is less than the temperature of extrusion apparatus 410. In some embodiments, the temperature of bath 460 is less than about 25° C. (e.g., less than about 15° C., less than about 10° C.). As an example, bath 460 can be at a temperature of from about 5° C. to about 10° C. (from about 6° C. to about 8° C.), such as about 7° C.

In general, the rate at which the tube is drawn through bath 460 can be varied as desired. In certain embodiments, the rate is at least about five feet per minute (e.g., at least about 10 feet per minute, at least about 20 feet per minute, at least about 30 feet per minute) and/or less than about 100 feet per minute (e.g., less than 90 feet per minute, less than about 80 feet per minute, less than about 70 feet per minute, less than about 60 feet per minute, less than about 50 feet per minute). For example, the rate can be from about 20 feet per minute to about 100 feet per minute (e.g., from about 30 feet per minute to about 50 feet per minute), such as about 30 feet per minute.

Steps 320, 330 and 340 can be performed using standard processes, such as disclosed, for example, in U.S. Pat. Nos. 5,195,969; 5,270,086 and 5,769,817, which are hereby incorporated by reference. As an example, during step 330 (which can occur before, during or after step 320), a temperature of at least about 120° C. and/or less than about 125° C. (e.g., about 123.5° C.) can be used for at least about three minutes and/or less than about five minutes (e.g., about four minutes). As another example, during step 340, the pressure may be at least about 200 psi to about and/or less than about 300 psi (e.g., from about 245 psi to about 265 psi), and the temperature may be at least about 90° C. and less than about 100° C. (e.g., from about 90° C. to about 95° C.).

Without wishing to be bound by theory, it is believed that optional mold heat set step 350 can assist in reducing (e.g., substantially eliminating) the presence of delamination in balloon 14.

The pressure used in step 350 is typically at least about 50 psi (e.g., at least about 100 psi, at least about 200 psi, at least about 225 psi) and/or less than about 400 psi (e.g., less than about 300 psi, less than about 275 psi), such as about 250 psi. The temperature of the balloon in step 350 is usually at least about 50° C. (e.g., at least about 150° C., at least about 125° C., at least about 140° C.) and/or less than about 250° C. (e.g., less than about 225° C., less than about 200° C., less than about 175° C., less than about 160° C.), such as from about 145° C. to about 150° C. The pressure and temperature are used for at least about five seconds (e.g., at least about 10 seconds, at least about 20 seconds) and/or at most about 50 seconds (e.g., at most about 40 seconds), such as about 30 seconds.

The following examples are illustrative only and not intended as limiting.

In the examples, the burst pressure of a balloon was determined as follows. The balloon was deflated and submerged in a water bath at 37° C. The balloon was then inflated with water at a rate of about 20 psi per second until the balloon burst. The rated burst pressure corresponds to the average pressure at which a balloon burst based on a given population of balloons (e.g., a population of about 30 balloons).

In the examples, the multiple inflation test of a balloon was performed as follows. The balloon was deflated and submerged in a water bath at 37° C. The balloon was inflated to the rated burst pressure of the balloon over the course of about 10 seconds, held at the rated bust pressure for about 30 seconds, and then deflated to a vacuum. A balloon was considered to have passed the multiple inflation test if the inflate/hold/deflate procedure was repeated 40 times with substantially no delamination or defect formation as determined by inspection with a microscope (10× magnification).

EXAMPLE 1

A three-layer balloon was prepared as follows.

A tube having layers formed of Melinar 5922C (E. I. DuPont de Nemours), Bynel CXA E-418 (E. I. DuPont de Nemours), and PEBAX 6333 (Atofina), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 550° F., 390° F., and 350° F., respectively. The pressures of the extruders were 2180-2240 psi, 1545-1550 psi, and 890-940 psi, respectively. The cooling bath temperature was 45° F., and the line speed was 90 feet per minute. The tube had an inner diameter of 0.0146 inch and an outer diameter of 0.0377 inch.

The tube was formed into a balloon using a balloon formation temperature of 95° C. and a balloon pressure of 140 psi. No heat set was used.

The balloon had a diameter of 3.0 millimeters, and a length of 20 millimeters. The overall single wall thickness of the balloon was 0.0007 inch. The balloon had a burst pressure of 374 psi (no observed delamination), and a compliance of 3.4%. Compliance was measured as follows. The balloon was held at 37° C. and inflated first to one atmosphere pressure, and then in increments of one atmosphere pressure while measuring the diameter of the balloon. This was done until the balloon reaches the rated burst pressure or until the balloon bursted. A plot of the results was generated, and the slope from four atmospheres pressure to the rated burst pressure was calculated, and was the compliance value (diameter versus pressure).

EXAMPLE 2

A three-layer balloon was prepared as follows.

A tube having layers formed of Melinar 5922C (E. I. DuPont de Nemours), Blox (Grade XU19080.01, Dow Chemical Company), and Vestamid L210F (Daicel-Degussa Ltd.), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 610° F., 350° F., and 495° F., respectively. The pressures of the extruders were 4610-4800 psi, 1052-1187 psi, and 2850-2980 psi, respectively. The cooling bath temperature was 45° F., and the line speed was 60 feet per minute. The tube had an inner diameter of 0.027 inch and an outer diameter of 0.063 inch.

The tube was formed into a balloon using a balloon formation temperature of 93° C. and a balloon pressure of 340 psi.

The heat set temperature was 170° C. The heat set pressure was 200 psi, and the heat set duration was 30 seconds.

The balloon had a diameter of 5.0 millimeters, and a length of 40 millimeters. The overall single wall thickness of the balloon was 0.0011 inch. The balloon had a burst pressure of 377 psi (no observed delamination), a compliance of 3.2% (measured as described in Example 1), and a maximum puncture force of 4.2 pounds.

EXAMPLE 3

A three-layer balloon was prepared as follows.

A tube having layers formed of Melinar 5922C (E. I. DuPont de Nemours), Bynel CXA E-418 (E. I. DuPont de Nemours), and PEBAX 7033 (Atofina), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 550° F., 390° F., and 400° F., respectively. The pressures of the extruders were 3020-3090 psi, 1110-1115 psi, and 970-1010 psi, respectively. The cooling bath temperature was 45° F., and the line speed was 30 feet per minute. The tube had an inner diameter of 0.039 inch and an outer diameter of 0.075 inch.

The tube was formed into a balloon using a balloon formation temperature of 95° C. and a balloon pressure of 255 psi. The heat set temperature was 170° C. The heat set pressure was 250 psi, and the heat set duration was 30 seconds.

The balloon had a diameter of 7.0 millimeters, and a length of 40 millimeters. The overall single wall thickness of the balloon was 0.0012 inch. The balloon had a burst pressure of 311 psi (no observed delamination), and a compliance of 3.5% (measured as described in Example 1).

EXAMPLE 4

A three-layer balloon was prepared as follows.

A tube having layers formed of Melinar 5922C (E. I. DuPont de Nemours), Bynel CXA E-418 (E. I. DuPont de Nemours), and PEBAX 7233 (Atofina), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 550° F., 390° F., and 400° F., respectively. The pressures of the extruders were 2970-3080 psi, 1330-1350 psi, and 790-840 psi, respectively. The cooling bath temperature was 45° F., and the line speed was 30 feet per minute.

The tube was formed into a balloon using a balloon formation temperature of 92° C. and a balloon pressure of 280 psi. The heat set temperature was 170° C. The heat set pressure was 200 psi, and the heat set duration was 30 seconds.

The balloon had a diameter of 7.0 millimeters, and a length of 20 millimeters. The overall single wall thickness of the balloon was 0.0012 inch. The balloon had a burst pressure of 296 psi. The balloon was exposed to the multiple inflation test and showed no signs of delamination (10× magnification) after bursting.

Nine balloons were prepared according to the same method. Each balloon was exposed to the multiple inflation test and showed no signs of delamination (10× magnification) after bursting.

EXAMPLE 5

A three-layer balloon was prepared as follows.

A tube having layers formed of Melinar 5922C (E. I. DuPont de Nemours), Bynel CXA E-418 (E. I. DuPont de Nemours), and Vestamid L2101F (Atofina), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 565° F., 300° F., and 350° F., respectively. The pressures of the extruders were 4020-4040 psi, 3130-3160 psi, and 2820-2900 psi, respectively. The cooling bath temperature was 45° F., and the line speed was 65 feet per minute.

The tube was formed into a balloon using a balloon formation temperature of 93° C. and a balloon pressure of 370 psi. The heat set temperature was 170° C. The heat set pressure was 270 psi, and the heat set duration was 30 seconds.

The balloon had a diameter of 5.0 millimeters, and a length of 40 millimeters. The overall single wall thickness of the balloon was 0.0013 inch. The balloon had a burst pressure of 406 psi. The balloon was exposed to the multiple inflation test and showed no signs of delamination (10× magnification) after bursting.

19 balloons were prepared according to the same method. Each balloon was exposed to the multiple inflation test and showed no signs of delamination (10× magnification) after bursting.

EXAMPLE 6

A three-layer balloon was prepared as follows.

A tube having layers formed of Melinar 5922C (E. I. DuPont de Nemours), Blox (Grade XU19080.01, Dow Chemical Company), and Vestamid L2101F (Atofina), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 540° F., 350° F., and 350° F., respectively. The pressures of the extruders were 6020-6210 psi, 3860-3870 psi, and 4070-5220 psi, respectively. The cooling bath temperature was 45° F., and the line speed was 70 feet per minute.

The tube was formed into a balloon using a balloon formation temperature of 93° C. and a balloon pressure of 360 psi. The heat set temperature was 170° C. The heat set pressure was 200 psi, and the heat set duration was 60 seconds.

The balloon had a diameter of 5.0 millimeters, and a length of 40 millimeters. The overall single wall thickness of the balloon was 0.0013 inch. The balloon had a burst pressure of 405 psi. The balloon was exposed to the multiple inflation test and showed no signs of delamination (10× magnification) after bursting.

Nine balloons were prepared according to the same method. Each balloon was exposed to the multiple inflation test and showed no signs of delamination (10× magnification) after bursting.

EXAMPLE 7

A three-layer balloon was prepared as follows.

A tube having layers formed of Melinar 5922C (E. I. DuPont de Nemours), Bynel CXA E-418 (E. I. DuPont de Nemours), and PEBAX 7233 (Atofina), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 550° F., 390° F., and 400° F., respectively. The pressures of the extruders were 2610-2700 psi, 1210-1225 psi, and 790-840 psi, respectively. The cooling bath temperature was 45° F., and the line speed was 34 feet per minute.

The tube was formed into a balloon using a balloon formation temperature of 93° C. and a balloon pressure of 265 psi. The heat set temperature was 170° C. The heat set pressure was 250 psi, and the heat set duration was 30 seconds.

The balloon had a diameter of 7.0 millimeters, and a length of 40 millimeters. The overall single wall thickness of the balloon was 0.0023 inch. The balloon had a burst pressure of 265 psi. The balloon was exposed to the multiple inflation test and showed no signs of delamination (10× magnification) after bursting.

Nine balloons were prepared according to the same method. Each balloon was exposed to the multiple inflation test and showed no signs of delamination (10× magnification) after bursting.

EXAMPLE 8

A three-layer balloon was prepared as follows.

A tube having layers formed of Melinar 5922C (E. I. DuPont de Nemours), Bynel CXA E-418 (E. I. DuPont de Nemours), and Vestamid L2101F (Atofina), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 550° F., 350° F., and 520° F., respectively. The pressures of the extruders were 5600-5840 psi, 3350-3384 psi, and 3910-3990 psi, respectively. The cooling bath temperature was 45° F., and the line speed was 50 feet per minute.

The tube was formed into a balloon using a balloon formation temperature of 93° C. and a balloon pressure of 380 psi. The heat set temperature was 180° C. The heat set pressure was 300 psi, and the heat set duration was 30 seconds.

The balloon had a diameter of 5.0 millimeters, and a length of 40 millimeters. The overall single wall thickness of the balloon was 0.0013 inch. The balloon had a burst pressure of 459 psi. The balloon was exposed to the multiple inflation test and showed no signs of delamination (10× magnification) after bursting.

Nine balloons were prepared according to the same method. Each balloon was exposed to the multiple inflation test and showed no signs of delamination (10× magnification) after bursting.

EXAMPLE 9

A three-layer balloon was prepared as follows.

A tube having layers formed of Melinar 5922C (E. I. DuPont de Nemours), Bynel CXA E-418 (E. I. DuPont de Nemours), and Vestamid L2101F (Atofina), respectively, was formed using an extrusion apparatus. The volumes of the portion of the cross-head containing the material was 3.7 cubic centimeters, 2.7 cubic centimeters, and 3.9 cubic centimeters, respectively. The temperatures of the extruders were 565° F., 250° F., and 520° F., respectively. The pressures of the extruders were 4220-4240 psi, 2000-2020 psi, and 2200-2280 psi, respectively. The cooling bath temperature was 45° F., and the line speed was 45 feet per minute.

The tube was formed into a balloon using a balloon formation temperature of 93° C. and a balloon pressure of 305 psi. The heat set temperature was 170° C. The heat set pressure was 200 psi, and the heat set duration was 30 seconds.

The balloon had a diameter of 8.0 millimeters, and a length of 40 millimeters. The overall single wall thickness of the balloon was 0.0013 inch. The balloon had a burst pressure of 316 psi. The balloon was exposed to the multiple inflation test and showed no signs of delamination (10× magnification) after bursting.

Nine balloons were prepared according to the same method. Each balloon was exposed to the multiple inflation test and showed no signs of delamination (10× magnification) after bursting.

While certain embodiments have been described, the invention is not limited to these embodiments.

As an example, the wall of the balloon can include additional layers so that the total number of layers in the wall exceeds three (e.g., at least four layers, at least five layers, at least six layers, at least seven layers, at least eight layers, at least nine layers, at least 10 layers, at least 15 layers, at least 20 layers, at least 30 layers, at least 40 layers, at least 50 layers).

As another example, layers 20, 22 and 24 need not be coextensive along their entire length. For example, there may be one or more interruptions (e.g., points of noncontact) between layers 20, 22 and/or 24.

In embodiments, a multilayer wall as described above can be attached to the surface of another, separately formed tube (e.g., by adhesive) which may be used in a medical device (e.g., a catheter body) or further processed (e.g., to form a balloon).

Furthermore, the balloons can be used in various medical procedures. As an example, the balloons can be used to open an occluded lumen, as in angioplasty. As another example, the balloons can be used to position another medical implement, such as a stent or graft, within a lumen. As an additional example, the balloons can be used to selectively block a passageway. In additional examples, the balloons can be used in various combinations of these procedures.

In addition, the methods can be used to form medical devices other than a balloon, such as a catheter shaft.

Other embodiments are in the claims.

The invention claimed is:

1. A medical device having a wall that comprises:
   a first layer including a first layer material selected from the group consisting of polyesters and polyester copolymers;
   a second layer including a second layer material selected from the group consisting of polyamides and polyamide copolymers; and
   a third layer including an adhesive material,
   wherein the first, second and third layers are coextruded.

2. The medical device of claim 1, wherein the third layer is between the first and second layers.

3. The medical device of claim 1, wherein the first layer is disposed along a first surface of the third layer, and the second layer is disposed along a second surface of the third layer.

4. The medical device of claim 1, wherein a thickness of the first layer is at least about 50 percent of a total thickness of the wall.

5. The medical device of claim 1, wherein a thickness of the second layer is less than about 20 percent of a total thickness of the wall.

6. The medical device of claim 1, wherein the adhesive material comprises an adhesive polymer.

7. The medical device of claim 6, wherein the adhesive polymer comprises an ethylene vinyl acetate polymer.

8. The medical device of claim 1, wherein the third layer has a thickness of less than about 0.005 inch.

9. The medical device of claim 1, wherein the medical device comprises a device selected from the group consisting of balloons, tubes and catheter shafts.

10. The medical device of claim 1, wherein the medical device comprises a balloon.

11. The medical device of claim 10, wherein the balloon has a diameter of at least about one millimeter.

12. The medical device of claim 1, wherein the first layer material and the second layer material are biaxially oriented.

13. A medical device having a wall that comprises:
a first layer including a first layer material selected from the group consisting of polyesters and polyester copolymers;
a second layer including a second layer material selected from the group consisting of polyamides and polyamide copolymers; and
a third layer including an adhesive material,
wherein the first, second and third layers are coextruded and a thickness of the first layer is at least about 50 percent of a total thickness of the wall.

14. The medical device of claim 13, wherein the thickness of the first layer is at least about 60 percent of the total thickness of the wall.

15. The medical device of claim 13, wherein the thickness of the first layer is at least about 70 percent of the total thickness of the wall.

16. The medical device of claim 13, wherein the third layer is between the first and second layers.

17. The medical device of claim 13, wherein the first layer is disposed along a first surface of the third layer, and the second layer is disposed along a second surface of the third layer.

18. The medical device of claim 13, wherein a thickness of the second layer is less than about 20 percent of the total thickness of the wall.

19. The medical device of claim 13, wherein the adhesive material comprises an adhesive polymer.

20. The medical device of claim 19, wherein the adhesive polymer comprises an ethylene vinyl acetate polymer.

21. The medical device of claim 13, wherein the third layer has a thickness of less than about 0.005 inch.

22. The medical device of claim 13, wherein the medical device comprises a device selected from the group consisting of balloons, tubes and catheter shafts.

23. The medical device of claim 13, wherein the medical device comprises a balloon.

24. The medical device of claim 23, wherein the balloon has a diameter of at least about one millimeter.

25. The medical device of claim 13, wherein the first layer material and the second layer material are biaxially oriented.

26. The medical device of claim 13, wherein the wall further includes additional layers of an adhesive material and additional layers comprising materials selected from the group consisting of polyesters, polyester copolymers, polyamides and polyamide copolymers,
wherein the layers in the wall are coextruded, and alternating layers of the wall comprise adhesive material.

27. A medical device having a wall that comprises:
a first layer including a first layer material selected from the group consisting of polyesters and polyester copolymers;
a second layer including a second layer material selected from the group consisting of polyamides and polyamide copolymers; and
a third layer including an adhesive material,
wherein the first, second and third layers are coextruded and a thickness of the third layer is less than about 20 percent of a total thickness of the wall.

28. The medical device of claim 27, wherein the thickness of the third layer is less than about 10 percent of the total thickness of the wall.

29. The medical device of claim 27, wherein the thickness of the third layer is less than about five percent of the total thickness of the wall.

30. The medical device of claim 27, wherein the third layer is between the first and second layers.

31. The medical device of claim 27, wherein the first layer is disposed along a first surface of the third layer, and the second layer is disposed along a second surface of the third layer.

32. The medical device of claim 27, wherein the adhesive material comprises an adhesive polymer.

33. The medical device of claim 32, wherein the adhesive polymer comprises an ethylene vinyl acetate polymer.

34. The medical device of claim 27, wherein the third layer has a thickness of less than about 0.005 inch.

35. The medical device of claim 27, wherein the medical device comprises a device selected from the group consisting of balloons, tubes and catheter shafts.

36. The medical device of claim 27, wherein the medical device comprises a balloon.

37. The medical device of claim 36, wherein the balloon has a diameter of at least about one millimeter.

38. The medical device of claim 27, wherein the first layer material and the second layer material are biaxially oriented.

39. The medical device of claim 27, wherein the wall further includes additional layers of an adhesive material and additional layers comprising materials selected from the group consisting of polyesters, polyester copolymers, polyamides and polyamide copolymers,
wherein the layers in the wall are coextruded, and alternating layers of the wall comprise adhesive material.

40. A medical device having a wall that comprises:
a first layer including a first layer material selected from the group consisting of polyesters and polyester copolymers;
a second layer including a second layer material selected from the group consisting of polyamides and polyamide copolymers; and
a third layer including an adhesive material,
wherein the first, second and third layers are coextruded and the third layer is less than about 0.005 inch thick.

41. The medical device of claim 40, wherein the third layer is less than about 0.004 inch thick.

42. The medical device of claim 40, wherein the third layer is less than about 0.003 inch thick.

43. The medical device of claim 40, wherein the third layer is between the first and second layers.

44. The medical device of claim 40, wherein the first layer is disposed along a first surface of the third layer, and the second layer is disposed along a second surface of the third layer.

45. The medical device of claim 40, wherein the adhesive material comprises an adhesive polymer.

46. The medical device of claim 40, wherein the adhesive polymer comprises an ethylene vinyl acetate polymer.

47. The medical device of claim 40, wherein the medical device comprises a device selected from the group consisting of balloons, tubes and catheter shafts.

48. The medical device of claim 40, wherein the medical device comprises a balloon.

49. The medical device of claim 48, wherein the balloon has a diameter of at least about one millimeter.

50. The medical device of claim 40, wherein the first layer material and the second layer material are biaxially oriented.

51. The medical device of claim 40, wherein the wall further includes additional layers of an adhesive material and additional layers comprising materials selected from the group consisting of polyesters, polyester copolymers, polyamides and polyamide copolymers, wherein the layers in the wall are coextruded, and alternating layers of the wall comprise adhesive material.

52. A medical device having a wall that comprises:

a first layer including a first layer material selected from the group consisting of polyesters and polyester copolymers;

a second layer including a second layer material selected from the group consisting of polyamides and polyamide copolymers; and a third layer including an adhesive material, additional layers of an adhesive material and additional layers comprising materials selected from the group consisting of polyesters, polyester copolymers, polyamides and polyamide copolymers, wherein the layers in the wall are coextruded, and alternating layers of the wall comprise adhesive material.

53. A medical device having a wall that comprises:

a first layer including a first layer material selected from the group consisting of polyesters and polyester copolymers;

a second layer including a second layer material selected from the group consisting of polyamides and polyamide copolymers; and a third layer including an adhesive material, additional layers of an adhesive material and additional layers comprising materials selected from the group consisting of polyesters, polyester copolymers, polyamides and polyamide copolymers, wherein the layers in the wall are coextruded, and alternating layers of the wall comprise adhesive material, and wherein a thickness of the first layer is at least about 50 percent of a total thickness of the wall.

54. A medical device having a wall that comprises:

a first layer including a first layer material selected from the group consisting of polyesters and polyester copolymers;

a second layer including a second layer material selected from the group consisting of polyamides and polyamide copolymers; and a third layer including an adhesive material, additional layers of an adhesive material and additional layers comprising materials selected from the group consisting of polyesters, polyester copolymers, polyamides and polyamide copolymers, wherein the layers in the wall are coextruded, and alternating layers of the wall comprise adhesive material, and wherein a thickness of the third layer is less than about 20 percent of a total thickness of the wall.

55. A medical device having a wall that comprises:

a first layer including a first layer material selected from the group consisting of polyesters and polyester copolymers;

a second layer including a second layer material selected from the group consisting of polyamides and polyamide copolymers; and a third layer including an adhesive material, additional layers of an adhesive material and additional layers comprising materials selected from the group consisting of polyesters, polyester copolymers, polyamides and polyamide copolymers, wherein the layers in the wall are coextruded, and alternating layers of the wall comprise adhesive material, and wherein the third layer is less than about 0.005 inch thick.

* * * * *